United States Patent
Kardassakis et al.

(10) Patent No.: US 9,780,554 B2
(45) Date of Patent: Oct. 3, 2017

(54) MOISTURE SENSORS

(71) Applicant: Apple Inc., Cupertinno, CA (US)

(72) Inventors: Peter J. Kardassakis, Cupertino, CA (US); Farhan Panthaki, Cupertino, CA (US); Samuel B. Weiss, Los Altos, CA (US)

(73) Assignee: Apple Inc., Cupertino, CA (US)

( * ) Notice: Subject to any disclaimer, the term of this patent is extended or adjusted under 35 U.S.C. 154(b) by 126 days.

(21) Appl. No.: 14/814,606

(22) Filed: Jul. 31, 2015

(65) Prior Publication Data

US 2017/0030851 A1    Feb. 2, 2017

(51) Int. Cl.
   *G01N 27/12*    (2006.01)
   *H02H 5/08*    (2006.01)

(52) U.S. Cl.
   CPC ......... *H02H 5/083* (2013.01); *G01N 27/121* (2013.01)

(58) Field of Classification Search
   CPC ............... G01N 27/22–27/24; G01N 27/121
   USPC .................................................. 324/664, 694
   See application file for complete search history.

(56) References Cited

U.S. PATENT DOCUMENTS

| | | | |
|---|---|---|---|
| 3,847,810 A * | 11/1974 | Tulumello | B01D 17/0202 210/391 |
| 3,950,627 A | 4/1976 | Murata et al. | |
| 4,552,570 A * | 11/1985 | Gravatt | G01N 27/225 95/10 |
| 5,041,330 A | 8/1991 | Heerten et al. | |
| 5,179,505 A | 1/1993 | Matsuo | |
| 5,258,592 A | 11/1993 | Nishikawa et al. | |
| 5,373,487 A | 12/1994 | Crawford et al. | |
| 6,112,580 A * | 9/2000 | Hesky | G01M 3/002 324/243 |

(Continued)

FOREIGN PATENT DOCUMENTS

| | | |
|---|---|---|
| CN | 102565149 | 7/2012 |
| CN | 105049966 | 11/2015 |

(Continued)

OTHER PUBLICATIONS

Bruno, Giuseppe; Foreign Priorty Application for Gruppo Sensori Incapsulato—IT 102015000019550; May 29, 2015; Ministero dello Sviluppo Economico.*

(Continued)

*Primary Examiner* — Melissa Koval
*Assistant Examiner* — Rahul Maini
(74) *Attorney, Agent, or Firm* — David K. Cole

(57) ABSTRACT

A moisture sensor includes one or more electrodes and sensor circuitry configured to detect the presence of moisture by detecting a change in an electrical measurement of the one or more electrodes. In response, the sensor may signal a component to perform an action. In some examples, capacitance and/or resistance between a pair of electrodes may be monitored, such as a pair of electrode sheets or meshes positioned in passage of a device that are separated by a gap. In various examples, a first electrode may be mounted cantilever to a second electrode and the presence of moisture between the electrodes may pull a free end closer to the second electrode. In some examples, the presence of moisture may cause bridging of a gap between two or more electrodes to complete or corrosion of a portion of an electrode to result in a change of resistance that can be detected.

21 Claims, 8 Drawing Sheets

(56) References Cited

U.S. PATENT DOCUMENTS

| | | | |
|---|---|---|---|
| 6,166,662 A | 12/2000 | Chuang | |
| 6,389,143 B1 | 5/2002 | Leedom et al. | |
| 6,501,036 B2 | 12/2002 | Rochon et al. | |
| 6,855,173 B2 | 2/2005 | Ehrnsperger et al. | |
| 6,963,039 B1 | 11/2005 | Weng et al. | |
| 7,230,196 B2 | 6/2007 | Toyama | |
| 7,355,137 B2 | 4/2008 | Kawasaki et al. | |
| 7,365,281 B2 | 4/2008 | Yamaguchi et al. | |
| 7,421,883 B2 * | 9/2008 | Khadkikar | G01N 27/227 73/31.05 |
| 7,461,560 B2 * | 12/2008 | Arms | G01N 27/223 73/765 |
| 7,580,533 B2 | 8/2009 | Schwartz | |
| 7,748,272 B2 | 7/2010 | Kranz et al. | |
| 7,764,936 B2 | 7/2010 | Nakasano et al. | |
| 7,865,210 B2 | 1/2011 | Wang et al. | |
| 8,059,490 B2 | 11/2011 | Rapps et al. | |
| 8,092,691 B2 | 1/2012 | Youngs et al. | |
| D653,640 S | 2/2012 | Kwon et al. | |
| 8,231,795 B2 | 7/2012 | Martin et al. | |
| 8,263,886 B2 | 9/2012 | Lin et al. | |
| 8,371,866 B1 | 2/2013 | Su et al. | |
| 8,381,575 B2 | 2/2013 | Seo | |
| 8,416,542 B2 | 4/2013 | Nakamura | |
| 8,446,713 B2 | 5/2013 | Lai | |
| 8,462,514 B2 | 6/2013 | Myers et al. | |
| 8,470,252 B2 | 6/2013 | Odueyungbo | |
| 8,482,305 B2 | 7/2013 | Johnson | |
| 8,526,175 B2 | 9/2013 | Yukawa et al. | |
| 8,562,095 B2 | 10/2013 | Alleyne et al. | |
| 8,591,240 B2 | 11/2013 | Jenks | |
| 8,614,897 B2 | 12/2013 | Tang | |
| 8,624,144 B2 | 1/2014 | Chiang | |
| 8,644,011 B2 | 2/2014 | Parkinson | |
| 8,683,861 B2 | 4/2014 | Humbert et al. | |
| 8,767,381 B2 | 7/2014 | Shukla et al. | |
| 8,770,996 B2 | 7/2014 | Hsu | |
| 8,800,764 B2 | 8/2014 | Wu | |
| 8,804,993 B2 | 8/2014 | Shukla et al. | |
| 8,826,558 B2 | 9/2014 | Priebe et al. | |
| 8,844,158 B2 | 9/2014 | Dehn | |
| 8,942,401 B2 | 1/2015 | Murayama | |
| 8,960,818 B2 | 2/2015 | Myers et al. | |
| 8,994,827 B2 | 3/2015 | Mistry et al. | |
| 9,013,888 B2 | 4/2015 | Trzaskos et al. | |
| 9,072,991 B2 | 7/2015 | Winters et al. | |
| 9,080,961 B2 | 7/2015 | Adachi | |
| 9,084,053 B2 | 7/2015 | Parkins | |
| 9,084,357 B2 | 7/2015 | Shedletsky et al. | |
| 9,099,264 B2 | 8/2015 | Shedletsky et al. | |
| 9,105,420 B2 | 8/2015 | Shah et al. | |
| 9,129,757 B2 | 9/2015 | Kanbayashi et al. | |
| 9,151,725 B2 * | 10/2015 | Fu | G01N 27/228 |
| 9,161,434 B2 | 10/2015 | Merz et al. | |
| 9,164,539 B2 | 10/2015 | Wu | |
| 9,171,535 B2 | 10/2015 | Abe et al. | |
| 9,226,076 B2 | 12/2015 | Lippert et al. | |
| 9,240,292 B1 | 1/2016 | Lapetina | |
| 9,253,297 B2 | 2/2016 | Abe et al. | |
| 9,506,888 B2 * | 11/2016 | Palazzotto | G01N 27/227 |
| 9,540,229 B2 * | 1/2017 | Bruno | B81B 7/0058 |
| 2006/0210062 A1 | 9/2006 | DeMichele et al. | |
| 2007/0003081 A1 | 1/2007 | Ram et al. | |
| 2007/0047747 A1 * | 3/2007 | Yoshida | H04R 3/007 381/189 |
| 2008/0302641 A1 | 12/2008 | Su | |
| 2009/0281251 A1 | 11/2009 | Bae et al. | |
| 2012/0067711 A1 | 3/2012 | Yang | |
| 2013/0037396 A1 | 2/2013 | Yu | |
| 2013/0146491 A1 | 6/2013 | Ghali et al. | |
| 2013/0170685 A1 | 7/2013 | Oh et al. | |
| 2013/0242481 A1 | 9/2013 | Kim et al. | |
| 2014/0029206 A1 | 1/2014 | Wittenberg et al. | |
| 2014/0218877 A1 | 8/2014 | Wei et al. | |
| 2014/0253150 A1 | 9/2014 | Menzel et al. | |
| 2015/0003213 A1 | 1/2015 | Suwald | |
| 2015/0153297 A1 * | 6/2015 | Aliane | G01N 27/223 73/335.04 |
| 2016/0052017 A1 | 2/2016 | Weber et al. | |
| 2016/0363555 A1 * | 12/2016 | Kang | G01N 27/227 |
| 2016/0377569 A1 * | 12/2016 | Rajaraman | G01N 27/223 257/416 |
| 2017/0016843 A1 * | 1/2017 | Gryska | G01N 27/226 |

FOREIGN PATENT DOCUMENTS

| | | |
|---|---|---|
| CN | 204906680 | 12/2015 |
| CN | 105323674 | 2/2016 |
| EP | 2326106 | 5/2011 |
| EP | 2640042 | 9/2013 |
| JP | S5620399 | 2/1981 |
| JP | 200353872 | 2/2003 |
| JP | 200483811 | 3/2004 |
| JP | 2004235724 | 8/2004 |
| JP | 2004244607 | 9/2004 |
| JP | 2012253426 | 12/2012 |
| WO | WO2012/117476 | 9/2012 |
| WO | WO2015/167848 | 11/2015 |

OTHER PUBLICATIONS

U.S. Appl. No. 14/040,386, filed Sep. 27, 2013, pending.
U.S. Appl. No. 14/474,435, filed Sep. 2, 2014, pending.
U.S. Appl. No. 14/695,357, filed Apr. 24, 2015, pending.
U.S. Appl. No. 14/805,035, filed Jul. 21, 2015, pending.
Author Unknown, "What to Do when Gadgets Get Wet," http://gadgetshow.channel15.com/gadget-show/blog/what-to-do-when-gadgets-get-wet, 2 pages, Aug. 23, 2010.

* cited by examiner

MOISTURE SENSORS

FIELD

The described embodiments relate generally to moisture detection. More particularly, the present embodiments relate to various moisture detection sensors positioned within an electronic device.

BACKGROUND

Many devices, such as smart phones, may be vulnerable to moisture, whether vapor or liquid form. Components such as housings, seals, and so on may be used to keep moisture away from moisture sensitive elements of the devices. However, such components may not keep out all moisture. This may particularly be the case where ports to an external environment are provided for device elements (such as ports for acoustic devices such as microphones or speakers), housing portions and/or other elements are joined at seams, and/or other such situations.

It may be useful to determine when a device and/or internal portions thereof is exposed to moisture. In some cases, a warrantee for a device may be voided if the device and/or internal portions thereof are exposed to moisture. In other cases, effectiveness of components such as housings or seals may be tested by determining whether or not moisture is present in internal portions of a device.

SUMMARY

The present disclosure describes systems, methods for, and apparatuses related to electrical moisture detection. A moisture sensor disposed in an interior of a device may include one or more electrodes and sensor circuitry configured to detect the presence of moisture by detecting a change in an electrical measurement of the one or more electrodes. In response to detection of moisture, the moisture sensor may signal a component of the device to perform one or more actions.

In some examples, capacitance and/or resistance between a pair of electrodes may be monitored to detect the presence of moisture. In one such example, a pair of hydrophobic coated electrode meshes may be positioned in an acoustic path of a device separated by a water absorbent material. In various examples, a first electrode may be mounted cantilever to a second electrode and the presence of moisture between the electrodes may pull a free end of the cantilever closer to the second electrode. In some examples, the presence of moisture may cause bridging of a gap between two or more electrodes to complete a circuit or corrosion of a portion of an electrode to open a circuit.

In various embodiments, an electronic device including a moisture sensor may include a housing, a first electrode sheet (such as a first mesh) positioned in a passage through the housing, a second electrode sheet (such as a second mesh) positioned in the passage and offset from the first electrode sheet by a gap, and sensor circuitry operatively coupled to the first and second electrode sheets. The sensor circuitry may be configured to detect a presence of moisture by detecting a change in an electrical measurement between the first and second electrode sheets.

In some examples, a moisture-absorbent substrate may be positioned in the gap that draws moisture away from the first or second electrode sheets. In various examples, the first electrode sheet and the second electrode sheet may be coated with hydrophobic coatings.

In one or more examples, the passage may be an acoustic path of the device, the acoustic path operatively coupled to an acoustic device and configured to pass acoustic signals. In other examples, the passage may be a barometric pressure vent for the device, the barometric pressure vent operatively coupled to an internal volume and configured to equalize internal pressure by allowing a flow of air into or out of the internal volume.

In various examples, the sensor circuitry may be configured to provide current to at least one of the first or second electrode sheets when the presence of moisture is detected to cause the at least one first and second electrode sheets to expand to reduce the liquid permeability of the first or second electrode sheets.

In some examples, the electrical measurement between the first and second electrode sheets may include a capacitance measurement and a resistance measurement and the device may be configured to characterize a type of the moisture or estimate a quantity of the moisture using the capacitance measurement and the resistance measurement.

In various examples, the sensor circuitry may be configured to signal the device based on the detection of the presence of moisture. In response to the signal, the device may perform an action. The action may include at least one of opening a vent to equalize internal pressure in an internal volume by allowing a flow of air or closing an air inlet valve to reduce ingress of moisture. In some examples, the device may perform the action in response to the signal upon computing an estimated quantity of the moisture based on the electrical measurement; and determining the estimated quantity is above a threshold value.

In some embodiments, a moisture sensor disposed in an interior of an electronic device may include a first electrode, a second electrode offset from the first electrode by a gap that is configured such that surface tension of moisture present in the gap causes at least a portion of the second electrode to deflect into the gap, and sensor circuitry operatively coupled to the first and second electrodes and configured to detect a presence of moisture by detecting a change in an electrical measurement between the first and second electrodes.

In various examples the second electrode may be mounted cantilever to the first electrode such that the second electrode has a fixed end and an unfixed end positioned over the first electrode. In some examples, the surface tension of the moisture present in the gap may bring the unfixed end closer to the first electrode. In one or more examples, the surface tension of the moisture present in the gap may cause the unfixed end to contact the first electrode.

In one or more embodiments, a moisture sensor disposed in an interior of an electronic device may include a substrate; a first electrode mounted on a surface of the substrate, a second electrode mounted on the surface of the substrate offset from the first electrode by a gap, and sensor circuitry operatively coupled to the first and second electrodes and configured to detect a presence of moisture by detecting a change in an electrical measurement between the first and second electrodes caused by conductive material bridging the gap.

In various examples, the conductive material may form in the gap as a result of the moisture. The conductive material may form in the gap as a result of corrosion of the first or second electrode caused by the moisture.

In some examples, the moisture sensor may further include a hydrophilic coating disposed in the gap that concentrates moisture for detection.

In various embodiments, a moisture sensor disposed in an interior of an electronic device may include a printed circuit board, a trace mounted on a surface of the printed circuit board that has a first portion and a second portion, and sensor circuitry operatively coupled to the trace and configured to detect a presence of moisture by detecting a change in resistance between the first portion and the second portion caused by corrosion.

In some examples, the change in resistance between the first portion and the second portion may result from corrosion of a third portion of the trace positioned between the first portion and the second portion caused by the presence of moisture. In various examples, the moisture sensor may further include a coating on the first portion and second portion that promotes corrosion of the third portion. In some examples, the third portion may a smaller height from the surface of the printed circuit board or a smaller width across the surface of the printed circuit board than the first portion and the second portion. In one or more examples, the moisture sensor may further include a hydrophilic coating disposed on the trace that concentrates moisture for detection.

BRIEF DESCRIPTION OF THE DRAWINGS

The disclosure will be readily understood by the following detailed description in conjunction with the accompanying drawings, wherein like reference numerals designate like structural elements.

DETAILED DESCRIPTION

Figure 1:
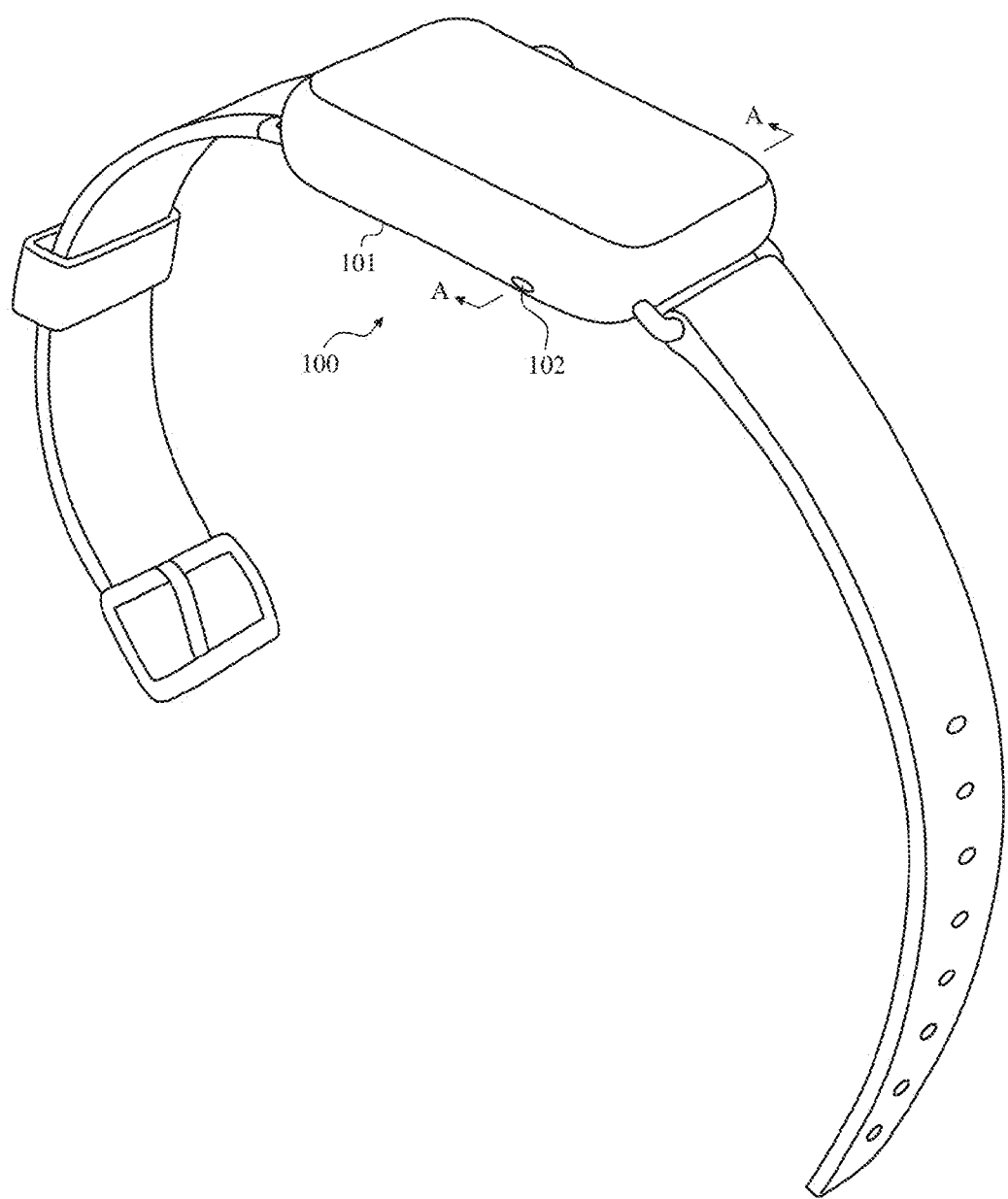
FIG. 1 shows a device that may include a moisture sensor.

Reference will now be made in detail to representative embodiments illustrated in the accompanying drawings. It should be understood that the following descriptions are not intended to limit the embodiments to one preferred embodiment. To the contrary, it is intended to cover alternatives, modifications, and equivalents as can be included within the spirit and scope of the described embodiments as defined by the appended claims.

The present disclosure describes systems, methods for, and apparatuses related to electrical moisture detection. A moisture sensor may include one or more electrodes and sensor circuitry configured to detect the presence of moisture by detecting a change in an electrical measurement (such as capacitance, resistance, and so on) of the one or more electrodes. The moisture sensor may be disposed in an interior of a device (such as a moisture vulnerable area like an acoustic path, a seam of a housing, proximate to moisture vulnerable components, and so on). In response to detection of moisture, the moisture sensor may signal a component of the device to perform one or more actions (such as opening a vent or other air outlet valve to equalize internal pressure in an internal volume by allowing the flow of air, closing an air inlet valve to reduce ingress of moisture, changing an operational state of the device, attempting to drive out the moisture such as by heating or producing tones, and so on).

In some examples, capacitance and/or resistance between a pair of electrodes may be monitored to detect the presence of moisture. In one implementation of such an example, a pair of electrode sheets (such as meshes) may be positioned in a passage (such as an acoustic path operatively coupled to an acoustic device and configured to pass acoustic signals) of a device separated by a gap. A water absorbent material may be positioned in the gap. The electrode sheets may be coated with hydrophobic coatings. Moisture on and/or between the electrode sheets may change a capacitance and/or resistance between the electrode sheets and may thus be detectable. In some cases, moisture between the electrode sheets may complete a circuit that passes current through the electrode sheets, causing the electrode sheets to expand and become less liquid permeable and/or become heated and thus evaporate moisture.

In various examples, a first electrode may be mounted cantilever to a second electrode. The presence of moisture between the electrodes may pull a free end of the cantilever (such as by surface tension) closer to the second electrode. The presence of moisture may be determined by detecting increase in proximity and/or contract between the two electrodes.

In some examples, the presence of moisture may cause bridging of a gap between two or more electrodes to complete a circuit or corrosion of a portion of an electrode to change a resistance that can be measured.

These and other embodiments are discussed below with reference to FIGS. 1-11. However, those skilled in the art will readily appreciate that the detailed description given herein with respect to these Figures is for explanatory purposes only and should not be construed as limiting.

FIG. 1 shows a device 100 that may include a moisture sensor. The device 100 may include one or more housings 101 and one or more entry points where moisture (such as water, water vapor, and so on) may enter the housing 101, such as a passage 102 through an aperture in the housing 101. One or more moisture sensors may be disposed in an interior of the housing 101. Such moisture sensors may include one or more electrodes and sensor circuitry configured to detect the presence of moisture by detecting a change in an electrical measurement of the one or more electrodes. In response to detection of moisture, the moisture sensor may, or cause the device 100 to, signal a component or subsystem to perform one or more actions.

Figure 2:
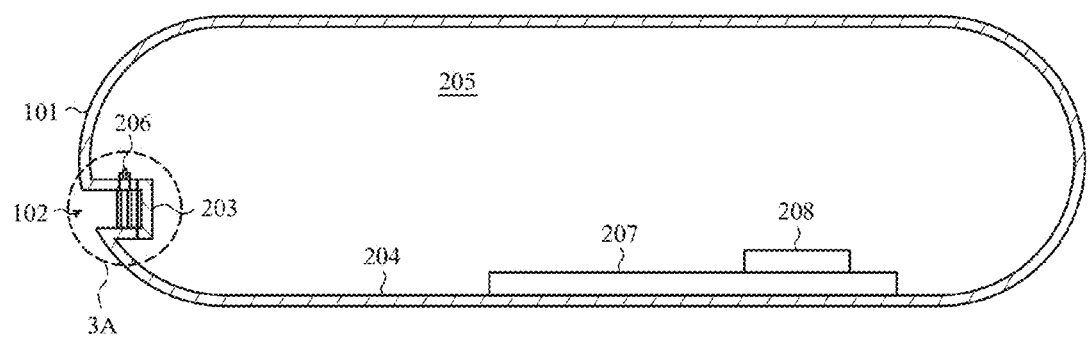
FIG. 2 shows a cross-sectional view of the device of FIG. 1 illustrating example moisture sensors, taken along line A-A of FIG. 1.

FIG. 2 shows a cross-sectional view of the device 100 of FIG. 1 illustrating example moisture sensors 206 and 208, taken along line A-A of FIG. 1. One or more such moisture sensors 206 or 208 may be disposed in a passage 102 (illustrated as an acoustic path for an acoustic device 203 that is operatively coupled to the acoustic device 203 and configured to pass acoustic signals), in an internal volume 205 of the housing 101 the device 100, on a printed circuit board 207 positioned on an internal surface 204 of the housing 101, and so on. The moisture sensors 206 or 208 may be disposed in moisture vulnerable areas (such as the passage 102, a seam of a housing 101, proximate to moisture vulnerable components such as components of the printed circuit board 207, and so on). In the illustration of FIG. 2, the size of the passage 102 is exaggerated in order to better illustrate various components and/or features.

Figure 3A:
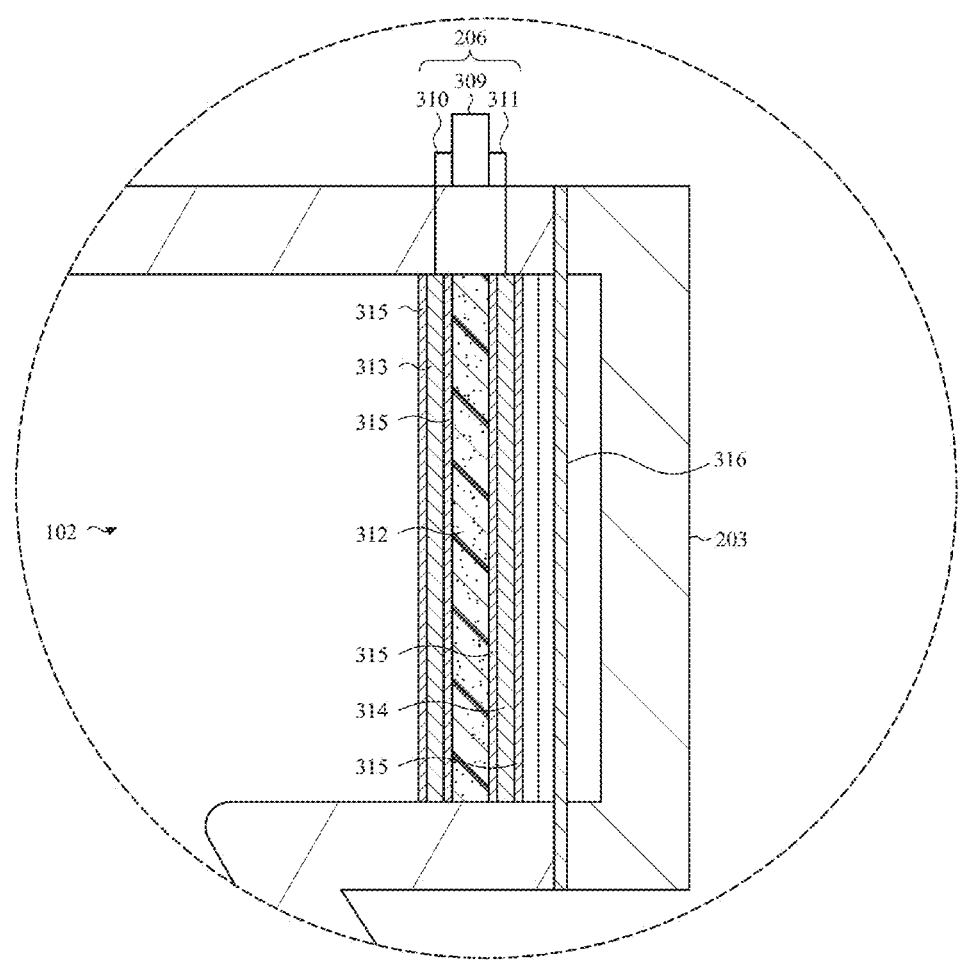
FIG. 3A is a detail view of an example implementation of the indicated portion of FIG. 2.

FIG. 3A is a detail view of an example implementation of the indicated portion of FIG. 2. The moisture sensor 206 may be positioned in the passage 102. As shown, the passage 102 is coupled to the acoustic device 203. In some implementations, a water resistant membrane 316 (such as expanded polytetrafluoroethylene) may be positioned between the moisture sensor 206 and the acoustic device 203.

Although the passage 102 is illustrated as an acoustic path for the acoustic device 203 that is operatively coupled to the acoustic device 203 and configured to pass acoustic signals, it is understood that this is an example. In some implementations, the passage 102 may be coupled to components other than an acoustic device 203, such as a barometric pressure vent, another kind of vent, any other component, or open directly into the internal volume 205 without connection to a component.

The moisture sensor 206 include a first electrode 313 and a second electrode 314 positioned in the passage 102. Positioning the first electrode 313 and the second electrode 314 in the passage 102 may include fully or partially disposing the first electrode 313 and the second electrode 314 within the passage 102, coupling the first electrode 313 and the second electrode 314 to an opening of the passage 102, and so on. The first electrode 313 and the second electrode 314 are illustrated as sheets of meshes, but may be any kind of electrodes such as copper, other conductive metals or other material, traces, and so on. The first electrode 313 and the second electrode 314 may be separated by a gap fully or partially filled by a moisture-absorbent material 312 (such as a foam, a wicking material, a desiccant such as silica gel, and/or any other moisture-absorbent substrate). The moisture-absorbent material 312 or other moisture-absorbent substrate may function to draw moisture away from the first electrode 313 and/or the second electrode 314. Sensor circuitry 309 may be configured to monitor one or more electrical measurements of the first and second electrodes 313 and 314 via conductive pathways 310 and 311.

For example, the sensor circuitry 309 may monitor a capacitance and/or a resistance between the first and second electrodes 313 and 314. The sensor circuitry 309 may determine that moisture is present if the monitored capacitance and/or resistance between the first and second electrodes 313 and 314 changes.

Figure 3B:
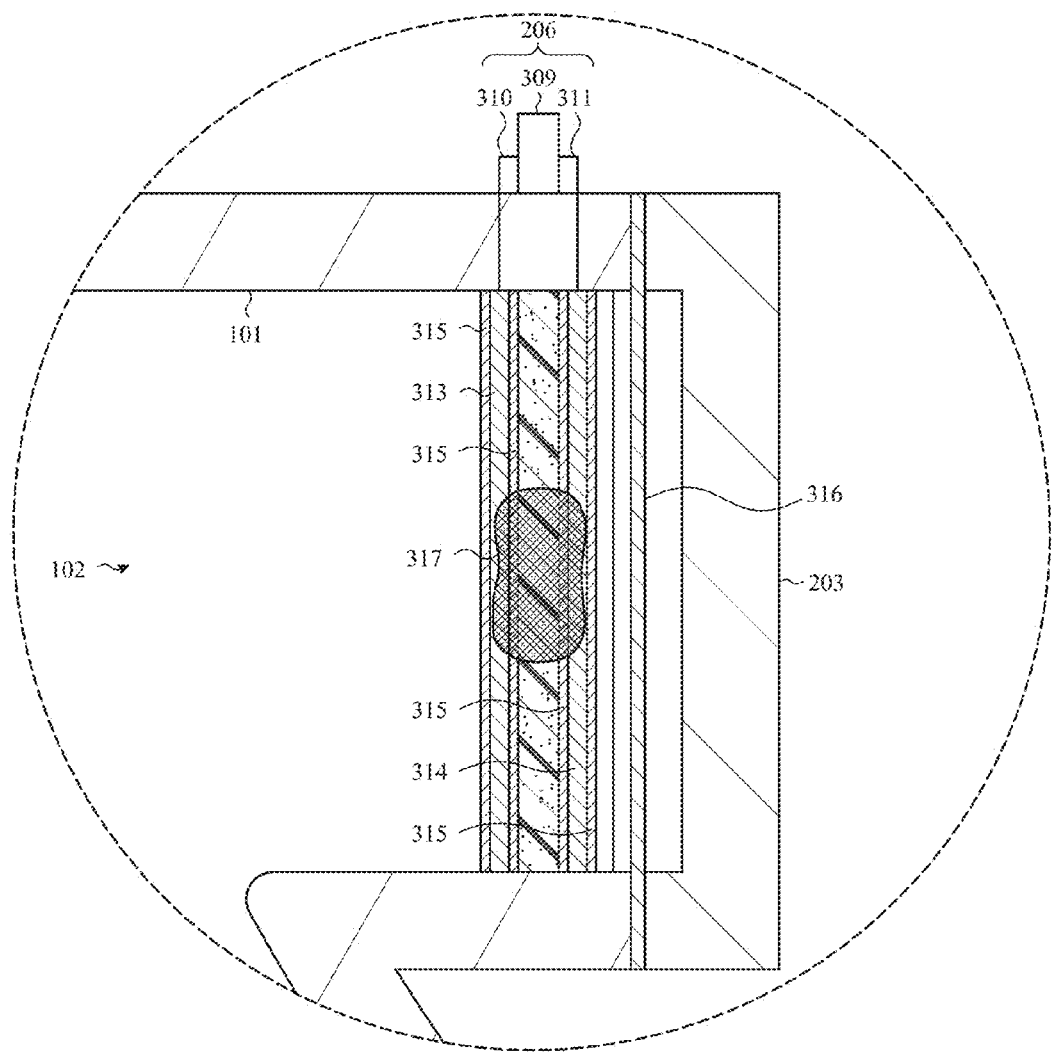
FIG. 3B shows the moisture sensor of FIG. 3A in the presence of moisture.

By way of example, the sensor circuitry 309 may measure a capacitance and/or a resistance between the first and second electrodes 313 and 314 in the absence of moisture as illustrated in FIG. 3A. FIG. 3B shows the moisture sensor 206 of FIG. 3B in the presence of moisture 317. As shown, the moisture 317 may be disposed on and/or between the first and/or second electrodes 313 and 314. This may change the capacitance and/or resistance between the first and second electrodes 313 and 314 monitored by the sensor circuitry 309. Based on this detected change, the sensor circuitry 309 may detect the presence of moisture.

For example, moisture 317 that contacts and/or is positioned between the first and/or second electrodes 313 and 314 may alter capacitance between the first and second electrodes 313 and 314. The higher the quantity of moisture 317 that is positioned between the first and second electrodes 313 and 314, the more that capacitance between the first and second electrodes 313 and 314 may change. By monitoring and measuring changes in the capacitance between the first and second electrodes 313 and 314, the sensor circuitry 309 may be able to detect the presence of moisture.

By way of another example, moisture 317 positioned on or between the first and/or second electrodes 313 and 314 may electrically connect the first and second electrodes 313 and 314, decreasing resistance between the first and second electrodes 313 and 314. The resistance change may vary by the quantity of moisture present. By monitoring and measuring changes in the resistance between the first and second electrodes 313 and 314, the sensor circuitry 309 may be able to detect the presence of moisture, characterize a type of the moisture, estimate a quantity of the moisture, and so on.

In some implementations, the first and/or second electrodes 313 and 314 may be coated with one or more hydrophobic coatings 315. Thus, in implementations where the moisture sensor 206 of FIG. 3A blocks the entirety or a majority of the passage 102, the moisture sensor 206 may function as a moisture barrier for the device 100. In such implementations, the hydrophobic coating 315 on the first electrode 313 may resist the passage of moisture in the direction of the moisture-absorbent material 312, the moisture-absorbent material 312 may resist the flow of moisture in the direction of the second electrode 314, and the hydrophobic coating 315 on the second electrode 314 may resist the flow of moisture in the direction of the water resistant membrane 316 and/or the acoustic device 203.

As shown, the moisture sensor 206 of FIG. 3A is shown as positioned to entirely block the passage 102. However, it is understood that this is an example. In various implementations, the moisture sensor 206 of FIG. 3A may be positioned such that it does not entirely block or block a majority of the passage 102 without departing from the scope of the present disclosure.

Figure 10:
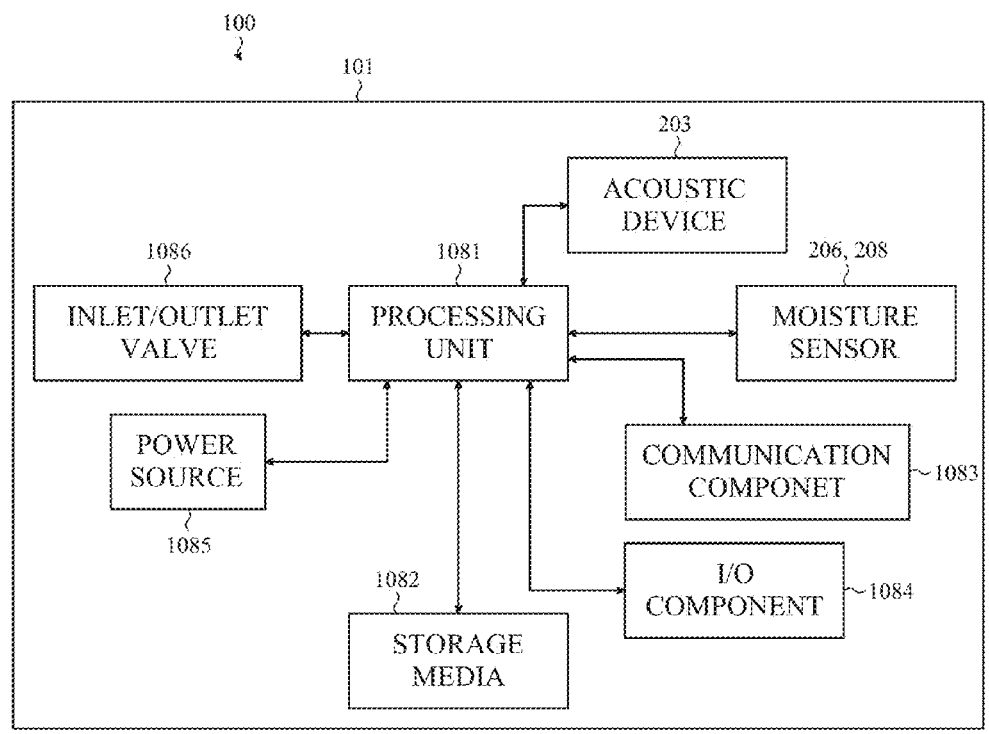
FIG. 10 shows a block diagram illustrating an example of relationships between example components of the device of FIG. 1.

In various implementations, the sensor circuitry 309 may transmit one or more signals to a component of the device 100 upon the detection of moisture (such as the processing unit 1081 of FIG. 10). Such signals may include indications that moisture is detected, data regarding the detection (such as the electrical measurements or changes), and so on).

In some cases, the sensor circuitry 309 and/or another component of the moisture sensor 206 may be directed in response to perform one or more actions related to the moisture. For example, the first and/or second electrodes 313 and 314 may be formed of materials configured to function as a heating element. The sensor circuitry 309 and/or another component may provide current that may be run through the first and/or second electrodes 313 and 314. This may cause the first and/or second electrodes 313 and 314 to heat to thermally drive off moisture. By way of another example, the first and/or second electrodes 313 and 314 may be formed of a material (such as nickel titanium, or nitinol) that is configured to expand. Current may be run through the first and/or second electrodes 313 and 314, which may cause the first and/or second electrodes 313 and 314 to expand, making it more difficult for moisture or liquid to pass through the moisture sensor 206 toward the acoustic device 203 and/or otherwise making the first and/or second electrodes 313 and 314 less permeable to liquid or moisture.

Although the above describes the moisture sensor 206 as being directed to perform the actions, in various implementations such actions may be performed passively. The presence of moisture on and/or between first and/or second electrodes 313 and 314 may complete a circuit and may thus cause current to run through the first and second electrodes 313 and 314, causing heating, expansion, and/or various other effects.

FIGS. 4A-8 show additional examples of moisture sensors 206 or 208 in accordance with further embodiments of the present disclosure.

Figure 4A:
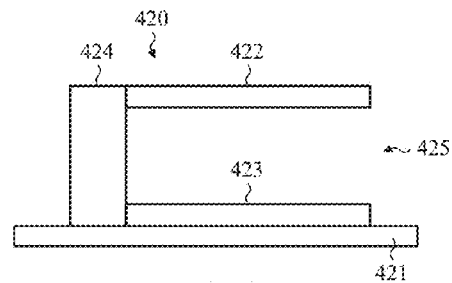
FIGS. 4A-8 shows additional examples of moisture sensors in accordance with further embodiments of the present disclosure.
Figure 4B:
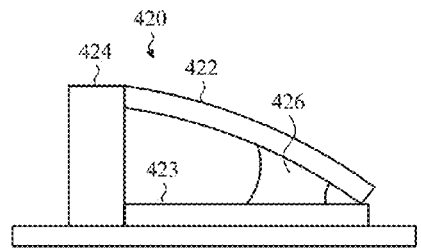

FIG. 4A shows an example moisture sensor 420 mounted to a substrate 421 (such as a silicon substrate, a printed circuit board, and so on) that includes a first electrode 422 and a second electrode 423 coupled to a mount 424. The first electrode 422 is mounted cantilever to the second electrode 423 such that the first electrode 422 has a fixed end coupled to the mount 424 and a free end positioned over the second electrode defining a gap 425 between the first electrode 422 and the second electrode 423. As shown in FIG. 4B, moisture 426 (e.g., a liquid droplet) may exert force (such as by surface tension of the moisture 426) to bring and/or otherwise pull the unfixed end of the cantilever closer to and/or in contact with the second electrode 423. In other words, with reference to FIGS. 4A and 4B, surface tension of moisture 426 present in the gap 425 causes at least a portion of the second electrode (the unfixed end) to deflect into the gap 425. By monitoring a change in an electrical measurement between the first and second electrodes 422 and 423 (such as resistance, capacitance, and so on), an increased proximity between the cantilever and the second electrode 423 and thus the presence of moisture 426 may be detected.

Figure 5A:
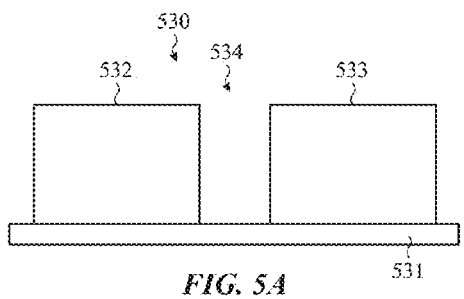
Figure 5B:
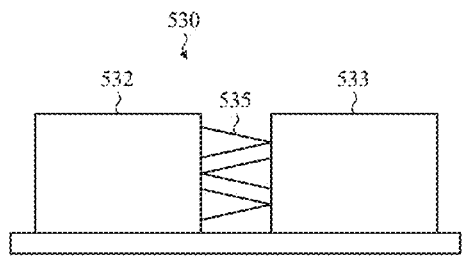

FIG. 5A shows another example moisture sensor 530 mounted to a substrate 531 that includes a first electrode 532 offset from a second electrode 533 by a gap 534. A resistance between the first and second electrodes 532 and 533 may be monitored for changes. As illustrated in FIG. 5B, the presence of moisture proximate to the moisture sensor 530 of FIG. 5B may cause the first and/or second electrodes 532 and 533 to corrode. With reference to FIGS. 5A and 5B, this corroded material may form dendrites 535 and/or other structures in the gap 534 that bridge the gap 534. Because this corroded conductive material forms in the gap 534 (bridging the gap 534 as a result of corrosion of the first and second electrodes 532 and 533 caused by the moisture), the resistance between the first and second electrodes 532 and 533 may change. Change in this resistance beyond a threshold (such as completion of the circuit between the first and second electrodes 522 and 523) may be detected as indicating the presence of moisture.

Formation of the corroded conductive material that bridges the gap 534 between the first and second electrodes 532 and 533 may not be reversible. As such, the moisture sensor 530 illustrated in FIGS. 5A and 5B may be "sacrificial" in that it may be used to detect whether or not the moisture sensor 530 has ever detected moisture but may not be able to detect whether or not moisture is currently present.

Figure 6A:
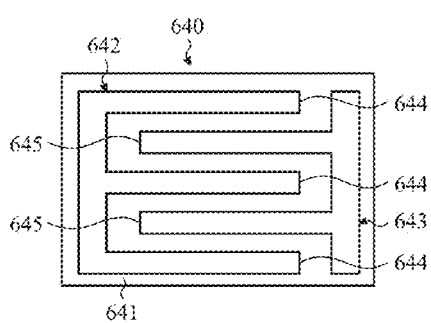
Figure 6B:
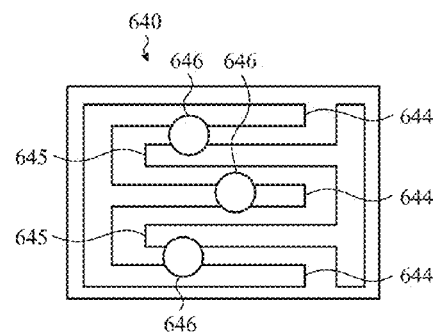

FIG. 6A shows still another example moisture sensor 640 mounted to a substrate 641 that includes a first array 642 of conductive materials 644 and a second array 634 of conductive materials 645, such as electrical traces formed on the substrate 641. The first and second arrays 642 and 643 are positioned such that the conductive materials 644 and 645 are offset from each other by gaps and are at least partially interposed with one another, forming a set of interlocking fingers. As shown in FIG. 6B, moisture 646 between and/or on one or more of the conductive materials 644 and/or 645 may change the dielectric constant of the gaps between the conductive materials 644 and/or 645. By monitoring the dielectric constant of the gaps and detecting a change in the monitored dielectric constant, the presence of moisture may be detected.

Figure 7A:
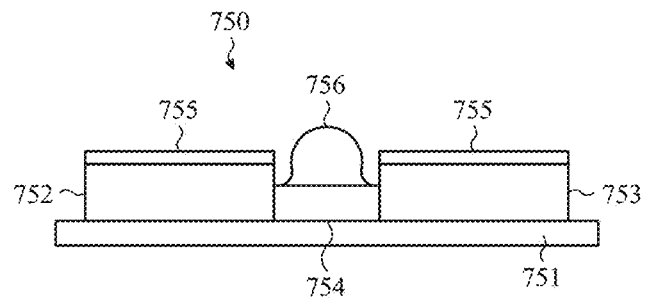
Figure 7B:
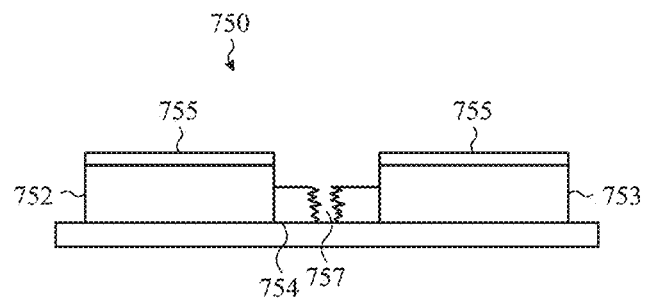

FIG. 7A shows yet another example moisture sensor 750 mounted to a substrate 751 that includes a trace or other electrode having a first portion 752 connected to a second portion 753 by a third portion 754. A resistance between the first portion 752 and the second portion 753 may be monitored. Moisture 756 that is present may corrode the third portion 754, as shown in FIG. 7B, and corrode a break 757 in the third portion 754, resulting in a change in the resistance between the first portion 752 and the second portion 753. Change in the resistance beyond a threshold (such as opening of the circuit between the first portion 752 and the second portion 753) may be detected as indicating the presence of moisture 756.

Like the moisture sensor 640 illustrated in FIGS. 6A and 6B, the moisture sensor 750 illustrated in FIGS. 7A and 7B may be sacrificial. As such, it may be used to detect whether or not the moisture sensor 750 has ever detected moisture but may not be able to detect whether or not moisture is currently present.

The first, second, and third portions 752, 753, and 754 are illustrated and described as separate components that may be differently dimensioned and may be made of different materials. For example, as illustrated the third portion 754 may have a smaller height from the surface of the substrate 751 or smaller width on the surface of the substrate 751 than either the first or second portions 752 and 753 such that it is configured to corrode more quickly than the first or second portions 752 and 753 in the presence of moisture. However, it is understood that this is an example. In various implementations, the first, second, and third portions 752, 753, and 754 may be identical regions of a single electrode through which current is passed from the first portion 752 to the second portion 753. In such an implementation, the third portion 754 may be any part of the electrode that corrodes to define the break 757.

Further, in some implementations the moisture sensor 750 illustrated in FIG. 7A may include one or more coatings 755 positioned on the first, second, and/or third portions 752, 753, and 754. Such a coating may be a hydrophobic coating or water barrier coating on the first and second portions 752 and 753 that encourages moisture 756 to collect and concentrate on the third portion 754, causing the third portion 754 to corrode faster than the first or second portions 752 and 753 to concentrate the moisture 756 for detection. Such a coating 755 may be a hydrophilic coating (such as positioned on the third portion 754 and/or the first, second, and third portions 752, 753, and 754) that attracts and concentrates the moisture 756 on the moisture sensor 750 such that smaller amounts of moisture will corrode the break 757 and are thus detectable than would in the absence of such concentration.

As illustrated, the coatings 755 are disposed on the first and second portions 752 and 753. However, it is understood that this is an example. In various other implementations, the coating 755 may be disposed on the third portion 754 and/or one or more coatings (hydrophobic coatings, hydrophilic coating, water barrier coatings, and so on) may be disposed on the first and/or second portions 752 and 753 to concentrate the moisture 756 on the third portion 754.

Figure 8:
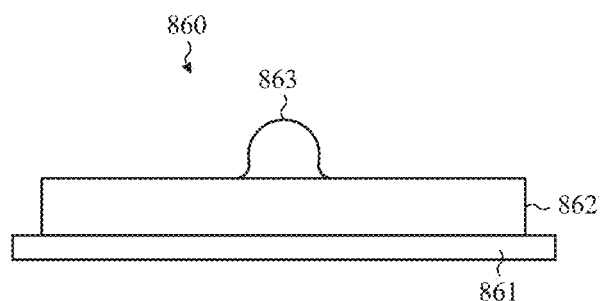
Figure 9:
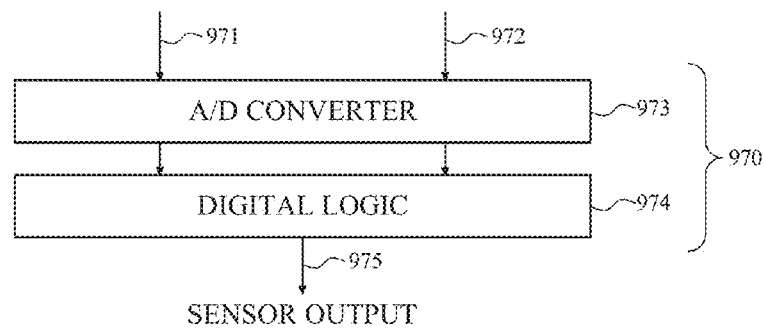
FIG. 9 is a schematic diagram of example circuitry that may be utilized to implement the sensor circuitry of FIG. 3A

FIG. 8 shows still another example moisture sensor 860 mounted to a substrate 861 that includes a single electrode 862. The electrode 862 may be used as a capacitive self-reference such that measurement of a capacitive loading of the electrode 862 is monitored. The presence of moisture 863 on and/or near the electrode 862 may change the capacitive loading of the electrode 862. As such, a change in the measured capacitive loading of the electrode 862 may be detected as indicating the presence of the moisture 863.

Although FIGS. 4A-8 illustrate the various example moisture sensors 420-860 mounted to substrates 421-861 in particular fashions, it is understood that these are examples. In various implementations, the various example moisture sensors 420-860 may be otherwise coupled to the respective substrates 421-861 (and/or one or more other substrates) in various orientations without departing from the scope of the present disclosure.

In various implementations, one or more of the moisture sensors 206, 208, and/or 420-860 illustrated and described above may be a microelectromechanical systems (MEMS) moisture sensor. Such a MEMS sensor may be incorporated into another component and/or MEMS component of the device 100, such as a MEMS acoustic device 203 (such as a MEMS microphone or speaker), a force sensor, and/or any other component.

FIG. 5 is a schematic diagram of example circuitry 970 that may be utilized to implement the sensor circuitry 407 of FIG. 4A. As shown, the sensor circuitry 970 may include an analog to digital converter 973 connected to the conductive pathways 971 and 972 (such as the conductive pathways 408 and 409), digital logic 974 connected to the analog to digital converter 973, and a sensor output line 975. The sensor circuitry 970 may be configured to detect a presence of moisture by detecting a change in an electrical measurement between the first and second electrodes (such as the first and second electrodes 401 and 402) connected to the conductive pathways 971 and 972. The sensor circuitry 970 may be so configured by the analog to digital converter 973 being configured to receive analog electrical signals regarding resistances and/or capacitances of the first and second electrodes via the conductive pathways 971 and 972, convert the electrical signals to digital values that the analog to digital converter 973 provides to the digital logic 974. The sensor circuitry 970 may be further so configured by the digital logic 974 being configured to evaluate the digital values provided by the analog to digital converter 973 to estimate a change in capacitance or resistance and/or determine whether or not a change has occurred and providing a sensor output accordingly via the sensor output line 975.

Similarly, circuitry 970 may be utilized with any of the example moisture sensors 420-860 of FIGS. 4A-8. In such implementations, the circuitry 970 may be connected to the various electrodes 422-423, 532-533, 642-643, 752,753, and 862 via the conductive pathways 971 and 972 such that the circuitry 970 may be operable to monitor the electrical properties of the electrodes 422-423, 532-533, 642-643, 752,753, and 862.

Referring again to FIGS. 1-2, although the device 100 is illustrated as a wearable device, it is understood that this is an example. In various implementations, the device 100 may be any device that may include a sensor positioned within or thereupon, such as a laptop computing device, a desktop computing device, a tablet computing device, a mobile computing device, a wearable device, a display, a speaker, an accessory, a digital media player, an input device, an output device, and so on.

Referring again to FIGS. 1-2, the device 100 may utilize the moisture sensor(s) 206 or 208 in a variety of ways. FIG. 10 shows a block diagram illustrating an example of relationships between example components of the device 100 of FIG. 1. For example, the may include one or more processing units 1081, non-transitory storage media 1082 (which may take the form of, but is not limited to, a magnetic storage medium; optical storage medium; magneto-optical storage medium; read only memory; random access memory; erasable programmable memory; flash memory; and so on), communication components 1083, input/output components 1084, power sources 1085, inlet/outlet valves 1086 (which may be a pressure vent operatively coupled to an internal volume 205 and configured to equalize internal pressure by allowing a flow of air into/out of the internal volume 205), acoustic devices 203, and moisture sensors 206 or 208 (or other moisture sensors). The processing unit 1081 may receive one or more signals from the moisture sensor(s) 206 or 208 (and/or sensor circuitry included therein) indicating the presence of moisture and may perform one or more actions based thereon. For example, the processing unit 1081 may open and/or close the inlet/outlet valve 1086 to block or reduce moisture ingress and/or let out pressure, cease providing power and/or reduce power provided from the power source 1085 to various components, transmit messages or provide notifications regarding the detected moisture via the communication component 1083 and/or the input/output component 1084, activate a heating element such as an element of the moisture sensor 206 or 208 or acoustic device 203 to drive off moisture, produce tones using the acoustic device 203 to drive out moisture, and so on.

The processing unit 1081 may be configured to compute and/or determine characteristics of present moisture based on data included in the signals from the moisture sensor(s) 206 or 208. For example, the data may include a capacitance measurement and a resistance measurement of one or more electrodes of the moisture sensor(s) 206 or 208 and the processing unit 1081 may use the capacitance measurement and the resistance measurement to compute or determine an estimated quantity of moisture present, a type of moisture present, and so on. The action(s) performed by the processing unit 1081 may be dependent upon the determined characteristics of the present moisture.

By way of example, any resistance change may indicate the presence of moisture but the magnitude of the capacitance change may indicate an amount of moisture present. Lower capacitance changes may indicate a smaller quantity of moisture present (such as a few drops of liquid from the moisture sensor 206 or 208 being splashed with a small quantity of liquid) whereas higher capacitance changes may indicate a larger quantity of moisture present (such as where the moisture sensor(s) 206 or 208 is submerged). In some cases, the processing unit 1081 may compute the estimated quantity and perform the action(s) only if the estimated quantity of moisture is above a threshold value, such as medium or high as opposed to low. This may allow the device 100 to perform actions in response to being submerged in liquid that should not be taken if the device 100 is merely splashed with liquid or is exposed to high humidity.

By way of another example, a higher resistance change may indicate the presence of moisture that is more conductive (such as salt water or sweat) whereas a lower resistance change may indicate the presence of moisture that is less conductive (such as fresh water or rain). In some cases, the processing unit 1081 may perform the action(s) only if the present moisture may be salt water as opposed to fresh water as salt water may be more corrosive to vulnerable components than fresh water. This may allow the device 100 to perform actions in response to being exposed to salt water that should not be taken if the device 100 is merely exposed to fresh water.

Figure 11:
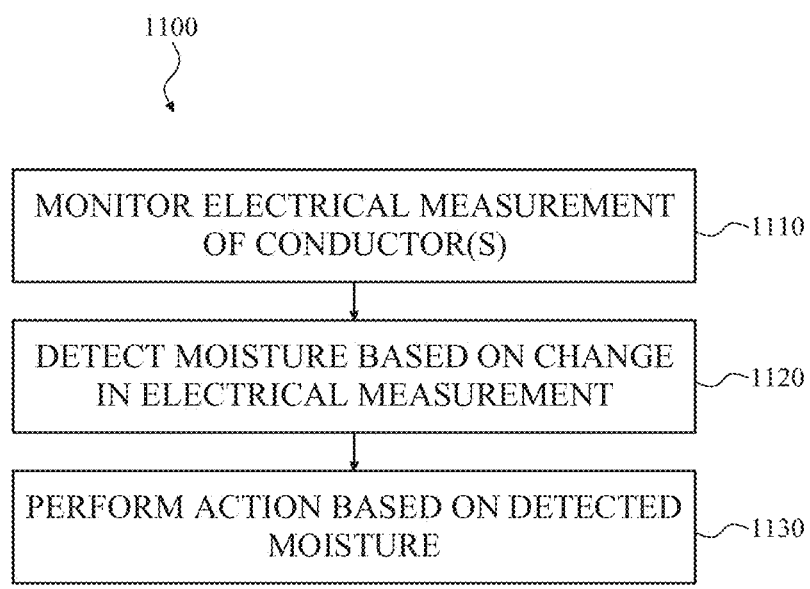
FIG. 11 shows a flow chart illustrating a method for detecting and responding to the presence of moisture. This method may be performed by and/or utilizing the devices and/or moisture sensors illustrated in FIGS. 1-10.

FIG. 11 shows a flow chart illustrating a method for detecting and responding to the presence of moisture. This method may be performed by and/or utilizing the devices and/or moisture sensors illustrated in FIGS. 1-10.

At 1110, an electrical measurement of one or more conductors may be measured. The measurement may include monitoring a circuit, capacitance or resistance between two electrodes, capacitive loading of an electrode, a dielectric constant in a gap between electrodes, and so on. The measurement may be an electrical measurement that changes in the presence of moisture.

At 1120, moisture may be detected based on a change in the monitored electrical measurement. For example, moisture may be detected based on opening or closing of a monitored circuit, a change in capacitance or resistance between two electrodes, a change in a capacitive loading of an electrode, a change in a dielectric constant in a gap between electrodes, and so on. In some implementations, moisture may be detected by comparing monitored multiple electrical measurements.

At 1130, an action may be performed based on the detected moisture. Such actions may include opening a vent or other air outlet valve to release pressure and/or equalize internal pressure in an internal volume by allowing a flow of air, closing an air inlet valve to block or reduce ingress of moisture, changing an operational state of the device (such as putting one or more components into a sleep and/or other low power state to reduce damage that could be caused by moisture), attempting to drive out the moisture such as by heating or producing tones, providing a notification that moisture has been detected, and so on.

Although the example method 1100 is illustrated and described as including particular operations performed in a particular order, it should be understood that this is an example. In various implementations, various orders of the same, similar, and/or different operations may be performed without departing from the scope of the present disclosure.

For example, the method 1100 is illustrated and described as performing an action based on the detected moisture. However, in some implementations moisture may be detected without performing any actions in response.

As described above and illustrated in the accompanying figures, the present disclosure describes systems, methods for, and apparatuses related to electrical moisture detection. A moisture sensor may include one or more electrodes and sensor circuitry configured to detect the presence of moisture by detecting a change in an electrical measurement (such as capacitance, resistance, and so on) of the one or more electrodes. The moisture sensor may be disposed in an interior of a device (such as a moisture vulnerable area like an acoustic path, a seam of a housing, proximate to moisture vulnerable components, and so on). In response to detection of moisture, the moisture sensor may signal a component of the device to perform one or more actions (such as opening a vent or other air outlet valve to equalize internal pressure in an internal volume by allowing a flow of air, closing an air inlet valve to reduce ingress of moisture, changing an operational state of the device, attempting to drive out the moisture such as by heating or producing tones, and so on).

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not target to be exhaustive or to limit the embodiments to the precise forms disclosed. It will be apparent to one of ordinary skill in the art that many modifications and variations are possible in view of the above teachings.

What is claimed is:

1. An electronic device comprising:
   a housing that defines an internal cavity of the electronic device, the housing having an opening;
   a moisture sensor comprising:
      a first electrode in the opening; and
      a second electrode in the opening interposed between the first electrode and the internal cavity, wherein the second electrode completely covers the internal cavity; and
   sensor circuitry in the housing that monitors an electrical measurement between the first and second electrodes, wherein the sensor circuitry is configured to detect moisture in the opening based on a change in the electrical measurement between the first and second electrodes.

2. The electronic device of claim 1, further comprising a moisture-absorbent substrate positioned between the first and second electrodes that draws moisture away from the first and second electrodes.

3. The electronic device of claim 1, wherein the first electrode is formed from a first mesh, and the second electrode is formed from a second mesh.

4. The electronic device of claim 1, wherein the first electrode and the second electrode are coated with hydrophobic coatings.

5. The electronic device of claim 1, further comprising:
   an acoustic device mounted in the internal cavity, wherein the acoustic device is configured to output acoustic signals through the internal cavity and opening.

6. The electronic device of claim 1, wherein the opening forms at least part of a barometric pressure vent that is coupled to the internal cavity, and the barometric pressure vent is configured to equalize internal pressure within the internal cavity by allowing air to flow into and out of the internal cavity.

7. The electronic device of claim 1, wherein the sensor circuitry is configured to provide current to the first electrode in response to detecting moisture in the opening, and wherein the current causes the first electrode to expand and reduce a permeability of the first electrode.

8. The electronic device of claim 1, wherein the sensor circuitry is configured to take a capacitive measurement and a resistive measurement between the first and second electrodes, the electronic device further comprising:
   processing circuitry configured to determine the amount of moisture in the opening using the capacitive measurement and the resistive measurement.

9. The electronic device of claim 1, further comprising a vent configured to equalize pressure in the internal cavity in response to the detection of the moisture by the sensor circuitry.

10. The electronic device of claim 1, further comprising an air inlet valve, wherein the air inlet valve is configured to close to reduce an ingress of moisture through the opening in response to the detection of the moisture by the sensor circuitry.

11. The electronic device of claim 1, wherein the moisture sensor is a microelectromechanical systems moisture sensor.

12. A moisture sensor comprising:
   a moisture-absorbent layer having first and second opposing surfaces;
   a first electrode mounted to the first surface of the moisture-absorbent layer;
   a second electrode mounted to the second surface of the moisture-absorbent layer; and sensor circuitry electrically connected to the first and second electrodes, wherein the sensor circuitry takes an electrical measurement between the first and second electrodes, wherein the sensor circuitry is configured to detect moisture on the first and second electrodes based on the electrical measurement, wherein the sensor circuitry is configured to provide current to the first and second electrodes, and wherein the moisture between the first and second electrodes shorts the first electrode to the second electrode and causes the current to pass through the first and second electrodes to thermally drive the moisture off of the first and second electrodes.

13. The moisture sensor of claim 12, wherein the current thermally drives the moisture off of the first and second electrodes by evaporating the moisture.

14. The moisture sensor of claim 12, wherein the electrical measurement is a resistive measurement.

15. The moisture sensor of claim 12, wherein the electrical measurement is a capacitive measurement.

16. The moisture sensor of claim 12, wherein the first and second electrodes are formed from copper.

17. An electronic device comprising:
a housing that defines an internal cavity of the electronic device, wherein the housing includes an opening;
a first electrode mounted in the opening;
a second electrode mounted in the opening between the first electrode and the internal cavity;
sensor circuitry electrically connected to the first and second electrodes, wherein the sensor circuitry detects moisture based on an electrical measurement between the first and second electrodes; and
an acoustic device in the internal cavity, wherein the acoustic device is configured to produce tones that drive the moisture out of the opening in response to the sensor circuitry detecting the moisture, wherein the second electrode is separated from the acoustic device by a gap.

18. The electronic device of claim 17, wherein the opening forms at least a portion of an acoustic passage for the acoustic device.

19. The electronic device of claim 17, further comprising a water resistant membrane between the second electrode and the acoustic device.

20. The electronic device of claim 17, wherein the first and second electrodes are coated with a hydrophobic coating.

21. The electronic device of claim 17, wherein a layer of moisture absorbent foam is interposed between the first and second electrodes.

* * * * *